(12) United States Patent
Opperman

(10) Patent No.: US 8,277,928 B2
(45) Date of Patent: Oct. 2, 2012

(54) ULTRA-THIN PHOTO-POLYMER COATINGS AND USES THEREOF

(75) Inventor: Gary Opperman, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 538 days.

(21) Appl. No.: 11/594,501

(22) Filed: Nov. 8, 2006

(65) Prior Publication Data

US 2010/0096320 A1      Apr. 22, 2010

Related U.S. Application Data

(60) Provisional application No. 60/734,961, filed on Nov. 8, 2005.

(51) Int. Cl.
*B32B 27/32* (2006.01)
*B32B 3/26* (2006.01)
*B32B 27/34* (2006.01)
*B32B 27/00* (2006.01)

(52) U.S. Cl. ............... 428/220; 428/332; 428/304.4; 428/474.4; 428/500

(58) Field of Classification Search .................. None
See application file for complete search history.

(56) References Cited

U.S. PATENT DOCUMENTS

| | | | |
|---|---|---|---|
| 5,629,084 A * | 5/1997 | Moya | 428/315.7 |
| 5,714,360 A | 2/1998 | Swan et al. | |
| 5,858,653 A | 1/1999 | Duran et al. | |
| 5,942,555 A * | 8/1999 | Swanson et al. | 522/35 |
| 6,007,833 A | 12/1999 | Chudzik et al. | |
| 6,077,698 A | 6/2000 | Swan et al. | |
| 6,121,027 A | 9/2000 | Clapper et al. | |
| 6,278,018 B1 | 8/2001 | Swan | |
| 6,506,895 B2 * | 1/2003 | Guire et al. | 536/25.32 |
| 6,689,473 B2 | 2/2004 | Guire et al. | |
| 2004/0137164 A1 * | 7/2004 | Swan et al. | 427/487 |
| 2005/0031793 A1 | 2/2005 | Moeller et al. | |
| 2005/0170071 A1 | 8/2005 | Eramo | |
| 2005/0232970 A1 * | 10/2005 | Stucke et al. | 424/426 |

FOREIGN PATENT DOCUMENTS

EP          1227120          7/2002

OTHER PUBLICATIONS

PCT International Search Report, Jul. 3, 2007 (6 pgs).

* cited by examiner

*Primary Examiner* — Sheeba Ahmed

(74) *Attorney, Agent, or Firm* — Kagan Binder, PLLC

(57) ABSTRACT

The invention provides methods for forming ultra-thin hydrophilic polymeric coatings on articles, as well as articles formed therefrom. The coatings are formed by irradiating a composition including a polymer having pendent photoreactive groups while the composition is in contact with a surface of the article.

40 Claims, No Drawings

ULTRA-THIN PHOTO-POLYMER COATINGS AND USES THEREOF

CROSS-REFERENCE TO RELATED APPLICATION

The present non-provisional application claims the benefit of U.S. Provisional Application having Ser. No. 60/734,961, filed on Nov. 8, 2005, and entitled, "Ultra-Thin Photo-Polymer Coatings and Uses Thereof"

FIELD OF THE INVENTION

The present invention relates to methods for forming extremely thin hydrophilic photo-polymeric coatings, microstructured or nano-structured articles having these coatings, and methods relating to the use of articles having these ultra-thin coatings.

BACKGROUND OF THE INVENTION

Materials that are used to fabricate articles that contact fluids, such as filters, biosensors, and implantable medical devices, are generally chosen for their bulk physical properties rather than for the properties these materials may confer to the article surface. As a result, while the object may have desirable properties such as strength and elasticity, its surface may not be optimized for interactions with fluids. Conventional methods and materials for the surface modification of such devices can be used, for instance, to decrease protein adsorption, increase wettability and lubricity, and decrease thrombus formation and bacterial colonization.

Conventional coating processes typically involve steps of preparing a coating composition that includes polymeric material, applying the compositions to the surface of a substrate, and then drying and curing the composition to form a polymeric coating on the surface of the substrate. In many coating procedures, coating compositions are applied to the surface by dip-coating or by spraying, and then are allowed to dry. However, these conventional coating techniques and reagents are frequently not well designed for applications that require very thin coatings. More typically these techniques result in coatings that are greater than 0.5 microns in thickness.

Various attempts have been made to provide passivated, biomolecule-compatible synthetic surfaces. These attempts have included the design and production of improved plastics, as well as the use of thin-film coatings of plastic, silica, semiconductor, and metal surfaces. Thin film coatings have tended to rely upon the adsorption and thermochemical bonding of preformed hydrophilic and surfactant polymers, in situ polymerization/crosslinking to form hydrophilic but insoluble polymeric films, or photochemical bonding of preformed hydrophilic and surfactant polymers after an article has been dip-coated in a coating solution.

Relatively thinner coatings can be prepared by vapor deposition polymerization (VDP). In VDP, monomer product is vaporized in a reaction chamber in the presence of a substrate. The vaporized monomer radical resublimates on the surface of the substrate, and reacts with other monomer radicals on the surface to form a thin polymer layer. Parylene™ (poly (para-xylylene)) coatings are commonly formed by VDP processes. Although these coatings are relatively very thin, they typically do not have thicknesses of less than 100 nm. Typically, poly(para-xylylene) coated layers are in the range of about 0.1 micron to about 75 microns in thickness. Even these relatively thin coatings that are formed by plasma deposition processes have the potential to provide coatings that may be too thick for some applications.

More recently, the preparation of "ultra-thin" coatings has been achieved. As referred to herein, "ultra thin" coatings can be considered to have a thickness of about 20 nm or less. Such ultra-thin coatings can be particularly useful for applications wherein a substantially thicker coating would otherwise obscure at least a part of the function of the device. These applications for "ultra thin" coatings are numerous and include, for example, coating surfaces that provide either small pore sizes or structural features of less than about one micron in size.

One general approach to providing an ultra-thin coating has been described in U.S. Pat. No. 6,689,473 (Guire et. al.) which describes forming an ultra-thin coating on a surface using amphiphilic-self assembling monolayer (SAM) molecules and latent reactive groups (such as photoreactive groups). The SAM molecules can be covalently coupled to a surface and/or coupled together to form a thin-coated layer on the surface of the article. These SAM-coated surfaces are useful for a number or purposes, including passivation against protein absorption and bacterial adherence, passivation against non-specific absorption on a biosensor, and preparation of an oligonucleotide array. Self-assembled monolayer ("SAM") technology has been used to generate monomolecular films of biological and non-biological (e.g., synthetic polymeric) molecules on a variety of substrates. The formation of such monolayer systems is versatile and can provide a method for the in vitro development of bio-surfaces which are able to mimic naturally occurring molecular recognition processes. SAMs also permit reliable control over the packing density and the environment of an immobilized recognition center or multiple centers, at a substrate surface.

Despite some progress, advancement in this technological area is still needed to provide ultra-thin coatings having properties such as complete and uniform surface coverage, hydrophilic properties, minimal nonspecific attraction for biomolecules and cells, sufficient stability and durability, broad applicability to various material surfaces, and ease and reproducibility for forming the coating. Furthermore, the coating should be easily formed by conventional manufacturing processes. In some cases it would also be desirable to prepare coatings that are resistant to conventional sterilization techniques that are used to prepare medical articles for use. In addition, it is also desirable to utilize coating materials that are not costly or that are relatively straightforward to synthesize.

What is clearly needed are methods and reagents for providing improved surface coatings, including those having further improved combinations of the various desirable properties listed above.

SUMMARY OF THE INVENTION

The present invention relates to forming ultra-thin hydrophilic photo-polymeric coatings on target surfaces. The ultra-thin polymeric coatings are useful in many applications, and can be formed to change or improve the properties of the target surface, or to provide a coated layer that is useful for the immobilization of other agents, for example, biological agents, such as proteins, nucleic acids, or cells.

Generally, according to the invention, the ultra-thin coatings are formed by preparing a coating solution that includes a hydrophilic photo-polymer (i.e., a hydrophilic polymer having pendent photoreactive groups) contacting the substrate with the coating solution, and then irradiating the substrate to promote formation of an ultra-thin polymeric layer on the surface of the substrate. The coating process is performed without drying down the coating solution on the surface of the substrate prior to the step of irradiating.

According to the methods of the present invention, it has been demonstrated that the ultra-thin photo-polymer layer formed on the surface can be less than 5 nm in thickness. However, thicker coatings using methods of the present invention can also be obtained, for example, by altering the coating parameters. In many of these cases, the resultant coatings can still be considered to be "ultra-thin" (less than 20 nm in thickness).

Despite the coatings being extremely thin, the coatings still provide desirable properties that are consistent with properties of the polymeric material of the coating. For example, an ultra-thin layer of hydrophilic polymer formed according to the invention shows excellent wettability characteristics.

The ultra-thin coatings described herein can be very useful when provided to the surface of articles having micro-structured or nano-structured features. In these cases, the overall function of the article in a particular application may necessitate that the coating is proportional to the features on the article. For example, an ultra-thin hydrophilic polymeric coating can be formed on a material having very small pores (e.g., a filter), such as less than 5 µm, and even less than 0.25 µM in size (250 nm) described herein. Because the photo-polymeric coating formed is so thin relative to the pore size, the pore size is not significantly reduced by formation of the coating, and therefore the performance of the substrate is not compromised. Other devices that the hydrophilic photo-polymers of the present invention can be applied to include, but are not limited to, molecular electronics, such as semiconductors fabricated from silicon materials, silver surfaces having organic molecules, chemically stable semiconductor layers, cluster/molecule/semiconductor assemblies, cluster networks, micro-electro-mechanical-systems (MEMS), actuators, micro-and nano-scale integrated systems, micro-fluidic bio-chips, micro-flow systems, and nano-electronic devices for DNA characterization.

In some aspects of the invention, the ultra-thin coating is formed on the surface of a textured or structured article, such as one selected from the group of articles having fibers, pores, filaments, threads, processes, apertures, or combinations thereof. One advantage of using the method of the invention is that the photo-polymer layer can be formed at one or more very specific and small locations on the surface of the device. That is, when the photo-polymer composition is in contact with the surface of the device, defined activating light irradiation can be applied to one or more very specific locations on the surface to provide an ultra thin coating at the specific location(s). In some cases, the irradiation pattern may correspond to the micro-or nano-structured surface of the device.

Surprisingly, it has also been found that even though the coatings described are extremely thin, they also have good durability. That is, the coating can be physically challenged and retain its hydrophilic properties following the challenge. This demonstrates that the coating that is formed, even though extremely thin, is very strong.

Another distinct advantage of the ultra-thin hydrophilic coatings of the invention relates to its ability to be rapidly and sufficiently hydrated. Thicker coatings may take a long time to wet, and thus take a long time to provide a hydrophilic surface, due to a greater amount of water that must be drawn into the coating. The ultra-thin coatings, however, are rapidly saturable.

This can be an advantage in forming a coating on a porous substrate. When exposed to a polar or aqueous liquid, a filter having an ultra-thin coating as described herein can rapidly be wetted and pass the liquid through the filter. The flux of the liquid is not hindered, and the filter is not subject to excessive pressure, which may be caused by a negative pressure (vacuum) or a forward pressure.

Another advantage of the present invention relates to methods for forming the ultra-thin coated layer, as in many aspects the coating can be rapidly and efficiently prepared. As demonstrated herein, a coating can be formed on the substrate by contacting the substrate with a coating solution (for example, by immersion) and irradiating the substrate in contact with the coating solution to form the coated layer. Steps that involve drying the coating composition are not required. This is in comparison to other coating processes that can require additional steps to prepare the coating. Furthermore, the supplemental addition of reagents, such as reagents that may be required to promote the formation of a polymeric coating, are not required. In turn, the inventive methods described herein are of economic advantage since there is a savings with regard to the time and reagents used in the coating process.

In some aspects of the invention, the substrate that is coated has a hydrophobic surface and also is a poor source of, or provides no abstractable hydrogens. In these aspects, it is thought that in preparing the ultra-thin coatings the photoreactive group of the photo-polymer promotes association with the substrate surface and then irradiation of the photoreactive groups promotes bonding between the photoreactive groups and portions of the polymer, which is a better source of abstractable hydrogen atoms as compared to the substrate surface. In this case, covalent bonds are predominantly formed between the photoreactive groups and the polymers of the coating composition to form an ultra-thin crosslinked network of hydrophilic polymers on the surface of the article.

Therefore, in some aspects, the invention provides an article having a hydrophilic polymeric coating having a thickness of 20 nm or less, the coating comprising a plurality of hydrophilic polymers covalently bonded via pendent photoreactive groups.

In some aspects, the invention provides a method for forming a hydrophilic coating on a surface of an article, the coating having a thickness of less than 20 nm. The method includes the steps of (a) contacting all or a portion of the article with a coating composition comprising a hydrophilic polymer comprising at least one pendent latent photoreactive group; and while the coating composition is in contact with the substrate, (b) irradiating the composition to activate the photoreactive groups to form the hydrophilic polymeric coating having a thickness of 20 nm or less.

In other aspects of the invention, a water soluble crosslinking agent that includes two or more pendent photoreactive groups is used to form the ultra thin coating. The crosslinking agent can be added to improve properties of the coating, such as durability. In forming the coating, the crosslinking agent can provide additional bonding between the hydrophilic polymers of the ultra-thin coated layer. For example, methods that utilize a crosslinking agent can include the steps of (a) contacting all or a portion of the article with a coating composition that includes (i) a hydrophilic polymer having pendent photoreactive groups and (ii) a water soluble crosslinking agent having pendent photoreactive groups; and while the coating composition is in contact with the surface of the article, and (b) irradiating the surface of the article.

In some aspects, the article has a surface that is hydrophobic and a poor source of abstractable hydrogens and is formed of a halogen-containing polymeric material, such as an article that is fabricated from a chloro-or fluoro-polymer. Exemplary polymeric materials include chloro-or fluoro-saturated polymers, such as PTFE.

In other aspects of the invention the ultra-thin hydrophilic coating is provided to an article having a porous structure. The article having a porous structure is preferably formed from hydrophobic material, and can optionally include material that provides sources of abstractable hydrogens.

Exemplary articles having porous surfaces include filters with small pore sizes. While the inventive hydrophilic coatings described herein can be useful for articles having any pore size, they are particularly useful for filters having pore sizes of about 5 microns or less, for example, having pore sizes ranging between about 0.05 microns and about 5 microns. The methods described herein can be performed to provide a hydrophilic coating to the surface of the filter wherein the coating does not compromise the performance of the filter. In some aspects the invention provides a filter comprising a hydrophilic photo-polymeric coating having a thickness of 20 nm or less and having an average pore size of 5 μm or less.

In a related aspect, the invention therefore also provides methods for the preparation of a filter having a hydrophilic coating, wherein the filter has a small pore sizes and wherein the hydrophilic coating does not significantly hinder the flux of fluid through the pores.

Also, according to some aspects of the invention, it has also been discovered that the use of hydrophilic polymers having a molecular weight of less than about 500 kDa can improve the formation and qualities of the ultra-thin coated layer. In some aspects hydrophilic polymers are used having a molecular weight in the range of about 10 kDa to about 500 kDa. Therefore, in another aspect, the invention provides a method for forming an ultra thin hydrophilic coating comprising the steps of (a) providing a coating composition that includes a hydrophilic polymer having pendent photoreactive groups, wherein the hydrophilic polymer has a molecular weight of 500 kDa or less, (b) contacting all or a portion of the article with the coating composition, and (c) irradiating the surface of the article while the coating composition is in contact with the surface of the article. The invention also contemplates articles having an ultra-thin coating of less than 20 nm formed from a hydrophilic polymer having a molecular weight of 500 kDa or less, or in some aspects in the range of 10 kDa to 500 kDa.

The hydrophilic polymer used to form the ultra thin coating includes two or more pendent photoreactive groups, and generally includes a plurality of pendent photoreactive groups. In some aspects, the hydrophilic polymer includes a plurality of photoreactive groups that are randomly spaced along the polymer backbone. Such polymers can be formed by the copolymerization of hydrophilic monomers and monomers having pendent photoreactive groups.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As used herein, the term "layer" or "coated layer" refers to a layer of one or more coated materials of sufficient dimensions (for example, thickness and area) for its intended use over the entire, or less than the entire, portion of an article surface. A "coating" as described herein can include one or more "coated layers," each coated layer including one or more coating components. In some aspects of the invention the coating consists of a single coated layer of photo-polymeric material.

The present invention is directed to methods for preparing coatings on surfaces of articles wherein it is desired to have an extremely thin hydrophilic polymeric layer, articles having extremely thin hydrophilic polymeric coatings, and also various methods for using these coated articles.

Since the ultra-thin coatings are particularly useful in a wide variety of applications, the invention is not limited to particular uses. Rather, the teachings of the invention demonstrate how the photo-polymeric coatings can be formed on a number of different articles that can be used in a variety of different applications. Based on this disclosure and the knowledge in the art, one would be able to form ultra-thin coating on a desired substrate to impart, for example, hydrophilic properties to the surface of the substrate.

In particular, the ultra-thin coatings of the invention are useful when it is desired to form a rapidly wettable, ultra-thin coating on the surface of an object. Therefore, the ultra-thin coatings can be used in areas of technology wherein the coated object is intended to come into contact with a polar fluid, such as water. Other exemplary fluids include buffers, beverages, and biological fluids.

In some aspects, the coatings of the present invention are used in areas of technology relating to the movement of fluids, such as water, including, but not limited to, fluid conduits, fluid filtration, microfluidics, biosensors, medical devices, etc. However, upon review of the disclosure, it will be apparent that the ultra-thin hydrophilic photo-polymer coatings of the present invention can be used in many different technological areas.

In some aspects of the invention, the ultra-thin coating is formed on the surface of a textured or structured article. Exemplary textured or structured article include those having fibers, pores, filaments, threads, processes, apertures, or combinations thereof. The ultra-thin coatings have been found to be particularly useful for coating articles having structural features ranging from nanometers to micrometers in size.

The ultra-thin hydrophilic photo-polymer layer can be formed on the surface of a device that includes any suitable substrate material. The materials from which a substrate or device is fabricated are referred to herein as "substrate material(s)" or "device material(s)." In some aspects the layer can be formed on devices or articles constructed from substantially all metal materials, such as alloys. The ultra-thin layer can also be formed on devices constructed from both non-metal and metal materials, for example, substrates having at least a portion of the surface including a metal. A metal surface can also be formed as a thin surface layer on a device formed from a non-metal material. Such surfaces can be formed by any method including sputter coating metal onto all or portions of the surface of the device.

Metals that can be used as substrate materials include platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can be suitable substrates to be used in a method of coating with the hydrophilic photo-polymers as described herein.

The surface of metal articles can optionally be treated to alter the surface chemistry. In many embodiments of the invention where it is desired to provide an ultra-thin hydrophilic photo-polymeric coating to a surface, it is preferred that if the surface chemistry is altered, it is done in such as manner as not to significantly add to the thickness of the material that will be applied to the surface (including the photo-polymer layer). For example, some metal or glass surfaces can be treated with a silane reagent, such as a hydroxy-or chlorosilane.

Other surfaces that can optionally be provided with an ultra-thin coating include those that comprise human tissue such as bone, cartilage, skin and teeth; or other organic materials such as wood, cellulose, compressed carbon, and rubber. Other contemplated materials include ceramics such as, but not limited to, silicon nitride, silicon carbide, zirconia, and alumina, as well as glass, silica, and sapphire. Combinations of ceramics and metals can also be coated.

The ultra-thin polymeric layer can be formed on the surface of plastic articles. "Plastic" is used in its broadest sense and includes all plastic substrates, including thermosets and thermoplastics. The plastic articles that are contemplated as substrates can range from very flexible plastic articles to very rigid plastic articles. In some aspects of the invention the ultra-thin hydrophilic photo-polymer coating is formed on a substrate that is somewhat rigid, or moderately rigid.

In some embodiments of the invention, the ultra-thin hydrophilic photo-polymeric coating is formed on the surface of a plastic substrate, wherein the plastic substrate includes a polymeric material that provides a poor source of, or no source of abstractable hydrogens. In these embodiments very little covalent coupling, or no covalent coupling, occurs between the hydrophilic photo-polymer and the surface of the device.

Surprisingly, it has been discovered that an ultra-thin coating having significant durability can be formed on these types of plastic surfaces. In these embodiments, it is speculated that the ultra-thin coating is formed by covalent coupling between hydrophilic photo-polymers via the photoreactive groups, thereby forming an extremely thin crosslinked network of photopolymers on the surface of the device. This type of layer formation can also be referred to as "inter-photo-polymer coupling".

As used herein, the term "durability" refers to the wear resistance of a polymer coating, or the ability of a coating to be maintained on a device surface when subjected to forces typically encountered during use (for example, normal force, shear force, and the like). A more durable coating is less easily removed from a substrate by abrasion. Durability of a coating can be assessed by subjecting the device to conditions that simulate use conditions. The ultra-thin coatings can be formed on the device surface in such a manner as to withstand the effect of shear forces that may be encountered in some aspects of the invention during use of the coated article. In these cases, such forces could otherwise result in delamination of the coating from the body member.

Another class of polymers that can be used as substrate materials include halogenated polymers, for example, chlorinated and/or fluorinated polymers. In some embodiments the substrate material includes a perhalogenated polymer. "Perhalogenated" refers to polymers wherein any carbon-bonded hydrogen is replaced by a halogen atom such as chlorine or fluorine. In some embodiments the substrate material includes a "perfluorinated" polymer, referring to polymers wherein all of the carbon-bonded hydrogens are replaced with fluorine. In some embodiments "partially fluorinated" polymers are used, referring to substrate polymers wherein not all carbon-bonded hydrogens are replaced by fluorine atoms, for example, at least one-fourth of the hydrogen atoms bonded to carbon atoms are replaced with fluorine atoms. A "fluorinated thermoplastic" refers to a fluoropolymer having a distinct melting point, as distinguished from amorphous materials such as fluoroelastomers that usually do not have such a melting point. A "thermoplastic elastomer" refers to a rubber-like material that can be process like thermoplastic materials.

Fluoroplastics can be useful as substrate materials because of properties they confer, such as chemical resistance properties. However, it is often difficult to covalently bond materials to the surface of substrates constructed from fluoropolymers because fluoropolymer-based substrates have surfaces that are poorly reactive or non-reactive. These fluoropolymers, including those commonly known under the trade name of Teflon™, have very lubricious and hydrophobic surface properties.

Examples of perhalogenated polymers that can be used as substrate materials include perfluoroalkoxy (PFA) polymers, such as Teflon™ and Neoflon™; polychlorotrifluoroethylene (PCTFE); fluorinated ethylene polymers (FEP), such as polymers of tetrafluoroethylene and hexafluoropropylene; poly(tetrafluoroethylene) (PTFE); and expanded poly(tetrafluoroethylene) (ePTFE). These polymers typically have melting temperatures ranging from about 100° C. to about 330° C.

Examples of partially fluorinated polymers include various combinations of interpolymerized units of TFE (tetrafluoroethylene), hexafluoropropylene (HFP), vinylidene fluoride (VDF), perfluoro alkyl or alkoxy vinyl ethers, and nonfluorinated olefins. Materials in this class include TFE/HFP/VDF copolymers such as THV (a polymer of tetrafluoroethylene, hexafluoropropylene and vinylidene fluoride), ETFE (a polymer of tetrafluoroethylene and ethylene), HTE (a polymer of hexafluoropropylene, tetrafluoroethylene, and ethylene), polyvinylidene fluoride (PVDF; such as Kynar™, Foraflon™, Solef™, Trovidur™), TFE/P (tetrafluoroethylene/propylene), and ethylene chlorotrifluoroethylene (ECTFE) copolymers, such as Halar™.

Other fluoropolymers are known in the art and described in various references, such as, W. Woebcken, Saechtling International Plastics Handbook for the Technologist, Engineer and User, $3^{rd}$ Ed., (Hanser Publishers, 1995) pp. 234-240.

To illustrate the use of a fluoropolymer as a substrate material according to the present invention and to demonstrate the advantages that the inventive coatings can provide to these types of substrates, the preparation of a hydrophilic coating of a photo-polymer on the surface of an ePTFE substrate is described.

ePTFE can be manufactured into a variety of substrate articles or devices useful in a wide variety of technologies. For example, ePTFE tubing is imparted with unique physical properties that make it ideal for use in medical devices, electronic insulators, high performance filters, and a number of other applications.

One particularly useful application involves coating a porous substrate, such as a filter, with a hydrophilic photo-polymer to form an ultra-thin hydrophilic layer. A filter substrate is described as it exemplifies an ideally suitable substrate for formation of an ultra-thin hydrophilic coated layer using the photo-polymers as described herein. Filters having the inventive ultra-thin coating can be employed for a variety of filtering applications, including fluid filtering. The term "filter" refers to any device that can block, trap, and/or modify particles or molecules passing through the device. A "fluid" refers to any form of readily flowing material, including liquids and gases. In some cases the filter can be an "active" filter, meaning that the filter is capable of action upon one or more components, or "target species," of a fluid stream, whether by catalysis, reaction, or some combination thereof, so that a modified specie(s) is formed. For example, in an active filter, a catalytic species can be coupled to the ultra-thin hydrophilic photo-polymeric layer.

In some aspects, in addition to pendent photoreactive groups, the hydrophilic polymer can also include pendent binding moieties. A "binding moiety" refers to any sort of chemical group that can bind or interact with a target species, such as an analyte, that is present in a sample (this may be more specifically referred to as a "target species binding moiety"). The binding moiety can include naturally occurring molecules or derivatives of naturally occurring molecules, or synthetic molecules, such as small organic molecules, or a larger synthetically prepared molecules, such as polymers. Examples of binding moieties include polypeptides, nucleic acids, polysaccharides, and portions of these types of molecules that can bind a target species. Hydrophilic polymers having pendent photoreactive groups and pendent binding moieties have been described in, for example, U.S. Pat. Nos. 5,858,653, and 6,121,027.

The ultra-thin hydrophilic photo-polymeric layer can be formed on the surface of an article having a "microporous substrate," referring to articles having pores on the order of about 0.05 µM to about 5 µm in width. Microporous substrates can include expanded microporous PTFE membranes.

Examples of suitable microporous layers include, but are not limited to, microporous ePTFE membranes, other polymeric (organic or inorganic) membranes, multi-layer membranes, filled membranes, asymmetric membranes, other non-woven or woven materials, and open cell foams.

Some conventional filters can be fabricated from felt and/or fabric materials, which can be prepared from a variety polymeric materials, and as described herein include fluoropolymers, aramids, and glasses. Selection of the type of materials used may be based on the liquid that is being filtered, as well as the operating conditions of the system and the type of particulates being filtered.

For example, PTFE membranes can be incorporated as surface laminates on conventional filter elements. Porous PTFE membranes can be prepared by a number of different known processes, such as by expanding PTFE as described in U.S. Pat. Nos. 4,187,390, 4,110,392 and 3,953,566, to obtain expanded, porous PTFE. Expanded PTFE (ePTFE) in the form of a membrane has a number of desirable properties that make it a particularly desirable filtration material. For example, ePTFE typically has many microscopic holes or "micropores", such as on the order of 0.05 µM to 10 µM across, which allow fluid molecules to pass through but restrict the passage of particulates, such as fine dust and the like. Additionally, the surface of an expanded PTFE membrane can be readily cleaned of accumulated contaminants, vastly improving the operative life of the filter.

The ultra-thin hydrophilic polymeric coating of the present invention can be particularly useful in filter technologies when it is desired to provide a hydrophilic surface on a filter that is fabricated from a material that is not hydrophilic. As discussed herein, the ultra-thin coatings can provide a number of advantages in this area, including providing a hydrophilic surface without significantly reducing pore size, providing a rapidly wettable hydrophilic surface, providing a durable coating, and forming a hydrophilic coating in a straightforward and efficient manner.

A filter having an ultra-thin hydrophilic photo-polymeric coating can also find use in a number of different technological areas. For example, these filters can be used in the electronics industry wherein there is a need for ultrapure, particle-free chemicals, such as solvents, acids, bases, ultrapure water, and photoresists. High purity reagents are very important in the production of DRAMs and many other critical microelectronic devices. Electronics grade chemicals and ultrapure water used in semiconductor manufacture are often filtered by microfilters to submicron levels, for removal of yield-damaging particulates. The coatings of the present invention can be used in conjunction with filters to provide these reagents of high purity.

In other embodiments of the invention, the ultra-thin hydrophilic photo-polymeric coating is formed on the surface of a plastic substrate, wherein the plastic substrate includes a polymeric material that provides a good source of abstractable hydrogens. That is, the polymeric material of the substrate can provide a surface to which the photo-polymer can react with, when activated. In these embodiments, the substrate includes one or more polymers that provide hydrogen atoms that are readily abstracted by an activated photoreactive group of the invention. For these substrates, the hydrophilic photo-polymer can become covalently coupled to the device surface via the photoreactive group. The extent of the covalent coupling may depend on various factors, including the amount and reactivity of abstractable hydrogens on the surface and the amount of photoreactive groups that are pendent from the hydrophilic photopolymer.

Plastic polymers include those formed of synthetic polymers, including oligomers, homopolymers, and copolymers resulting from reactions such as addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, polyhexamethylene dodecanediamide, and also polyurethanes, polycarbonates, polyamides, polysulfones, poly(ethylene terephthalate), polydimethylsiloxanes, and polyetherketone.

Other suitable polymers for the substrate material include polyamides, polyimides, polyolefins, polystyrenes, polyesters, polycarbonates, polyketones, polyureas, acrylonitrile butadiene, butadiene rubber, chlorinated and chloro-sulfonated polyethylene, chloroprene, EPM ((poly)ethylene propylene terpolymer), EPDM (ethylene-propylene-dicyclopentadiene copolymer), PE/EPDM blends (polyethylene/ethylene-propylene-dicyclopentadiene copolymer), PP/EPDM blends (polypropylene/ethylene-propylene-dicyclopentadiene copolymer), EVOH (ethylene vinyl alcohol polymer), epichlorihydrin, isobutylene isoprene, isoprene, polysulfides, silicones, NBR/PVC (acrylonitrile rubber/PVC blend), styrene butadienes, vinyl acetate ethylenes, and combinations thereof.

In yet other embodiments, the inventive ultra-thin coatings can be used in conjunction with microfluidic devices. Microfluidic devices are typically characterized by having one or more fluid channels with at least one dimension of less than 1 mm. Fluids that are commonly used in microfluidic devices include whole blood samples, protein or antibody solutions, nucleic acid solution, prokaryotic or eukaryotic cell suspensions, and various buffers. Microfluidic devices having ultra-thin photo-polymeric coatings can be used in methods to measure various parameters including fluid viscosity, pH, molecular diffusion coefficients, chemical binding coefficients, and enzyme reaction kinetics. Microfluidic devices can also be used for flow cytometry, DNA and/or RNA analysis, capillary electrophoresis, isoelectric focusing, immunoassays, sample injection of proteins for analysis via mass spectrometry, PCR amplification, cell manipulation, cell separation, cell patterning, and chemical gradient formation. The coated devices can be used for any form of research, and can also be used in clinical diagnostics.

Examples of microfluidic separation devices, particularly chip-based, micromachined capillary electrophoresis (CE) systems are described in U.S. Pat. Nos. 5,904,824, 6,068,752 and 6,103,199.

The use of ultra-thin coatings for microfluidic devices can be very desirable because the volume of fluids within these channels can be very small, for example, in the nanoliter range, and the amount of reagents and analytes used can also be quite small. In many cases expensive reagents or valuable samples are used in these devices. The ultra-thin coatings of the invention can therefore improve the function of the microfluidics device by, for example, improving the flow of fluids in the microfluidics channels, decreasing non-specific absorption of proteins in the channels, improving the viability of cells in the channels, and improving chemical separation. These improvements may result in a decrease in the quantity of reagents that are needed for a certain process, thereby resulting in savings in overall time and cost associated with any particular microfluidics process.

An ultra-thin coating of photo-polymer can be formed on the microfluidics channel in the following manner. The device is filled with a coating composition including the hydrophilic polymer having photoreactive groups and then the coating composition is treated with irradiation to form an ultra-thin coated layer. Alternately, the coating can be formed on the channels prior to assembly of the device.

In yet other embodiments, the inventive coatings can be used in conjunction with biosensors. Biosensors are devices that provide molecular recognition of one or more biological material(s), such as proteins, enzymes, antibodies, DNA, RNA, or microorganisms. Generally, biosensors are useful for identifying and quantifying a target moiety against other moieties present in a sample liquid. Specifically, the biological material included in the sample is quantified by utilizing a reaction that is caused when the biological material is recognized by a binding member.

Enzyme biosensors are typically used to detect substances such as creatinine, glucose, lactic acid, cholesterol, and amino acids, and are utilized for medical diagnostics or in the food industry. A prototype biosensor is the amperometric glucose sensor. Many enzyme-based biosensors operate by promoting the chemical reduction of an electron transfer agent by the specific reaction of a target component in a biological sample with an enzyme that is specific for the target component. The amount of biological material (substrate) in a biological sample is determined via a quantification apparatus which electrochemically measures a reduction quantity of the transfer agent, thereby performing quantitative analysis of the specimen. Biosensors can include electrochemical cells in which there can be working electrodes, counter electrodes, and reference electrodes. Biosensors can also include reactions that promote electrochemiluminescence (ECL) (see, for example, U.S. Pat. No. 6,852,502).

Electrochemical biosensors are known. They have been used to determine the concentration of various analytes from biological samples, particularly from blood. Examples of electrochemical biosensors are described in U.S. Pat. Nos. 5,413,690, 5,762,770, 5,798,031, and 5,997,817.

The ultra-thin hydrophilic photo-polymeric coatings of the present invention can be formed on the surface of the biosensor to improve various aspects of the biosensor function, including sensitivity and specificity.

For example, an ultra-thin coated layer of hydrophilic polymeric material can be formed on the hydrophobic surface of a biosensor. Normally, a hydrophobic surface may cause the accumulation of plasma proteins on the biosensor electrode, leading to denaturing of the proteins and formation of protein deposits. These deposits can affect the performance of the sensor through physical interference.

The ultra-thin hydrophilic photo-polymeric coatings can reduce the electrode impedance of the biosensors by allowing the formation of a hydrophilic surface via the ultra-thin photo-polymeric coating, thereby promoting unimpeded water movement on the surface of the sensor.

Furthermore, because the coating is particularly thin, the function of any binding members on the surface of the device will not be significantly compromised.

One type of biosensor the ultra-thin hydrophilic polymeric coating can be formed on is a waveguide sensor, or a biosensor that has waveguide sensor features. Optical waveguide sensors can be used to detect and/or measure analytes on a waveguide surface based on the detection of a refractive index change. Planar optical waveguides can function as optical sensors that detect changes in the media surrounding the waveguide, as the electromagnetic field propagating in the waveguide will extend into the surrounding media as an evanescent electromagnetic field. Exemplary waveguide sensors include grating-based waveguide sensors, Using the methods of the invention, an ultra-thin coating can be formed on the surface of the waveguide, thereby allowing analyte binding to occur very close to the surface. Since the sensitivity of these types of detectors is closely linked to the distance between the surface of the sensor and the bound analyte, an ultra-thin coating of hydrophilic polymers with attached analyte offers the passivation benefits provided by the properties of the coated hydrophilic polymer while improving sensitivity by reducing the distance between the waveguide surface and the bound analyte. Waveguide sensors can be used for various types of detection and/or measurement including cells, proteins and peptides, drugs, small organic molecules, such as glucose, nucleic acids, and carbohydrates.

In yet other embodiments, the ultra-thin hydrophilic photo-polymeric coatings is formed on all or a portion of the surface of a medical article. The medical article can be any that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

The inventive coating compositions can be utilized to coat virtually any medical article for which it is desired to provide a functional coating at a surface thereof. Exemplary medical articles include drug-delivering vascular stents (e.g., self-expanding stents typically made from nitinol, balloon-expanded stents typically prepared from stainless steel); other vascular devices (e.g., grafts, catheters, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder and renal devices, and catheters); colostomy bag attachment devices; ophthalmic devices; glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts).

Other devices include urinary catheters (e.g., surface-coated with antimicrobial agents such as vancomycin or norfloxacin), intravenous catheters (e.g., treated with antithrombotic agents (e.g., heparin, hirudin, coumadin), small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, benign prostate and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Other devices include, but are not limited to, vena cava filters, urinary dialators, endoscopic surgical tissue extractors, atherectomy catheters, clot extraction catheters, percutaneous transluminal angioplasty catheters (PTCA catheters), stylets (vascular and non-vascular), guidewires (such as coronary guidewires and peripheral guidewires), drug infusion catheters, esophageal stents, circulatory support systems, angiographic catheters, transition sheaths and dilators, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Other devices suitable for the present invention include, but are not limited to, implantable vascular access ports, blood storage bags, blood tubing, intraaortic balloon pumps, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices").

An ultra-thin hydrophilic photo-polymeric coating of the invention can be particularly useful for those medical devices that will come in contact with aqueous systems, such as bodily fluids. In some aspects, an ultra-thin hydrophilic layer improves the biocompatibility of the device surface and can minimize adverse reactions that may impair function of the coated device in the body.

The ultra-thin hydrophilic photo-polymeric coating is formed using a hydrophilic polymer having pendent photoreactive groups. The hydrophilic polymer that is used to form the ultra-thin layer, for example, can be a copolymer or a homopolymer. As used herein, the term "hydrophilic" refers to a polymer that does not repel water molecules. Hydrophilic polymers typically are soluble in water.

The hydrophilic polymer that is used to form the ultra-thin coating can be a synthetic polymer, a natural polymer, or a derivative of a natural polymer. Exemplary natural hydrophilic polymers include carboxymethylcellulose, hydroxymethylcellulose, derivatives of these polymers, and similar natural hydrophilic polymers and derivatives thereof.

In some embodiments the hydrophilic polymer that includes pendent photoreactive groups is synthetic. Synthetic hydrophilic polymers can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

In some embodiments, the hydrophilic photo-polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of hydrophilic monomers. Exemplary hydrophilic monomers include (meth)acrylamide and (meth)acrylamide derivatives, such as alkyl(meth)acrylamide and aminoalkyl (meth)acrylamide, such as aminopropylmethacrylamide and dimethylaminopropylmethacrylamide. Use of PVP copolymers is particularly advantageous for the preparation and use of PVP that is derivatized with photoreactive groups.

Vinyl pyrrolidone copolymers can be prepared in order to provide a photo-polymer with a specific property. For example, poly(vinylpyrrolidone-co-vinyl acetate) polymers can be prepared to alter their relative hydrophilicity, and to change the properties of the film in accordance with its desired use.

Methods for the preparation of PVP as well as photo-PVP are known in the art (see U.S. Pat. No. 6,077,698). PVP can be prepared by the polymerization of 1-vinyl-2-pyrrolidone in water using hydrogen peroxide as an initiator. Methods for terminating the polymerization VP can allow the preparation of PVP of desired molecular weights.

According to the invention, it has also been discovered that polymers having a molecular weight of about 500 KDa or less are able to provide a very effective ultra-thin hydrophilic coating. That is, hydrophilic polymers of this size can be formed into an ultra-thin coating having properties in accordance with preferred embodiments of the invention, such as wettability and durability. In some aspects, the hydrophilic polymers of the invention have a weight average molecular weight ($M_w$) size in the range of about 10 kDa to about 100 kDa, and in other aspects in the range of about 10 kDa to about 75 kDa.

As used herein "weight average molecular weight" or $M_w$, is an absolute method of measuring molecular weight and is particularly useful for measuring the molecular weight of a polymer, such as a preparations of photo-polymers as described herein. Polymer preparations typically include polymers that individually have minor variations in molecular weight. Polymers are molecules that have a relatively high molecular weight and such minor variations within the polymer preparation do not affect the overall properties of the polymer preparation (for example, the characteristics of a photo-polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

In another embodiment of the invention the ultra-thin hydrophilic photo-polymeric layer is formed from a coating composition that includes two or more hydrophilic polymers, at least one of which has pendent photoreactive groups. Optionally, the ultra-thin layer can be formed from a coating composition that includes two hydrophilic photo-polymers. In some aspects at least one of the two hydrophilic polymers is poly(vinylpyrrolidone).

If two or more hydrophilic polymers are used in the coating composition, in some aspects, at least one of the polymers has a $M_w$ of about 500 kDa or less, or in the range of about 10 kDa to about 500 kDa. If two or more hydrophilic polymers are used in the coating composition, in some aspects both have a $M_w$ of about 500 kDa or less, or in the range of about 10 kDa to about 500 kDa.

Photoreactive groups are pendent from the hydrophilic polymer and are activated during the coating process in order to form the ultra-thin coating. Generally, a photoreactive group that is "pendent" from the hydrophilic polymer is arranged on the polymer in a manner so that it can be activated using light energy and bond to a moiety, such as a photopolymer and/or a substrate material.

The photoreactive groups can be pendent along the length of the polymer and spaced along the length of the polymer in a random or ordered manner. It is speculated that photoreactive groups spaced along the length of the polymer allow the photo-polymer to associate with the surface prior to irradiation in a manner that promotes the formation of an ultra thin coatings according to the methods described herein.

Photoreactive groups, broadly defined, are groups that respond to specific applied external light energy to undergo active specie generation with resultant covalent bonding to a target. Photoreactive groups are those groups of atoms in a molecule that retain their covalent bonds unchanged under conditions of storage but which, upon activation, form covalent bonds with other molecules. The photoreactive groups generate active species such as free radicals, nitrenes, carbenes, and excited states of ketones upon absorption of external electromagnetic or kinetic (thermal) energy. Photoreactive groups may be chosen to be responsive to various portions of the electromagnetic spectrum, and photoreactive groups that are responsive to ultraviolet, visible or infrared portions of the spectrum are preferred. Photoreactive groups, including those that are described herein, are well known in the art. The present invention contemplates the use of any suitable photoreactive group for formation of the inventive coatings as described herein.

Photoreactive groups can generate active species such as free radicals and particularly nitrenes, carbenes, and excited states of ketones, upon absorption of electromagnetic energy. Photoreactive groups can be chosen to be responsive to various portions of the electromagnetic spectrum. Those that are responsive to the ultraviolet and visible portions of the spectrum are typically used.

Photoreactive aryl ketones such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives can be used. Examples of aryl ketones include heterocyclic derivatives of anthrone, including acridone, xanthone, and thioxanthone, and their ring substituted derivatives. Some photoreactive groups include thioxanthone, and its derivatives, having excitation energies greater than about 360 nm.

These types of photoreactive groups, such as aryl ketones, are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides [(RO)$_2$PON$_3$] such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetatoacetates (—CO—$CN_2$CO—O—) such as t-butyl alpha diazoacetoacetate.

Other photoreactive groups include the diazirines (—$CHN_2$) such as 3-trifluoromethyl-3-phenyldiazirine; and ketenes (CH=C=O) such as ketene and diphenylketene.

A hydrophilic photo-polymer can be formed using any sort of synthetic process that will result in the formation of a hydrophilic polymer with one or more pendent photoreactive groups. For example, a hydrophilic photo-polymer can be synthesized by attaching photoreactive groups to a "pre-formed" hydrophilic polymer. The preformed polymer can be obtained from a commercial source or be synthesized from the polymerization of a desired monomer or combination of different monomers. In one example of preparing the photo-polymer, a compound that includes a photoreactive group and a first reactive group is reacted with a portion of a hydrophilic polymer that is reactive with the first reactive group, resulting in the formation of a hydrophilic polymer having a pendent photoreactive group. The reaction preferably does not result in the activation of the photoreactive group; therefore the photoreactive group remains "latent" and capable of activation by actinic radiation during the coating process. Such attachments of the photoreactive group can be achieved by, for example, substitution or addition reactions.

For example, in one embodiment, the polymeric portion of the photo-polymer is formed by reacting acrylamide, 2-acrylamide-2-methylpropane sulfonic acid, and N-(3-aminopropyl)methacrylamide. In another embodiment, the polymeric portion is prepared by the copolymerization of 1-vinyl-2-pyrrolidone and N-(3-aminopropyl)methacrylamide. The copolymers are derivatized with an acyl chloride (such as, for example, 4-benzoylbenzoyl chloride) under Schotten-Baumann conditions to form photo-poly(vinylpyrrolidone) (also referred to as "photo-PVP"). That is, the acyl chloride reacts with the amino group of the N-(3-aminopropyl) moiety of the copolymer. An amide is formed resulting in the attachment of the aryl ketone to the polymer. The liberated hydrochloric acid is neutralized with an aqueous base solution.

In another method of preparing the photopolymer, monomers having photoreactive groups are obtained or prepared. These monomers are then co-polymerized with other monomers that do not have photoreactive groups to create a photopolymer. This is a particularly suitable way for preparing photopolymers that have desired amount of photoreactive groups, and desired monomeric units. A useful polymerizable mixture of monomers for preparation of the photopolymer includes, for example, from about 0.1% to about 10% of a photoreactive group-monomer, and from about 90% to about 99.9% of a hydrophilic monomer, or combination of hydrophilic monomers, as based on a molar percentage of the total amount of monomers present in the mixture. The photo monomers used to prepare the photopolymer can include any suitable polymerizable portion, such as, for example, acrylic monomers, vinyl monomers, or ether monomers.

In one exemplary method of synthesis, photo-polyacrylamide is prepared by copolymerizing methacrylamide having a photoreactive group with acrylamide. The photo-methacrylamide monomer can be prepared according to the process described in U.S. Pat. No. 6,007,833 (see Examples 1 & 2). Specifically, a methacrylamide-oxothioxanthene monomer (N-[3-(7-methyl-9-oxothioxanthene-3-carboxamido) propyl]methacrylamide (MTA-APMA)) can be prepared by reacting 7-methyl-9-oxothioxanthene-3-carboxylic acid chloride (MTA-Cl) with N-(3-aminopropyl)methacrylamide hydrochloride (APMA). MTA-APMA can then be copolymerized with acrylamide in DMSO in the presence of a chain transfer agent, a co-catalyst, and a free radical initiator. MTA-APMA can also be copolymerized with other types of monomers, such as vinyl pyrrolidone, to produce other photo-polymers (see also U.S. Pat. No. 6,007,833).

In order to provide a substrate with an ultra-thin hydrophilic photo-polymeric coated layer, the hydrophilic photo-polymer is provided in a coating composition. The coating composition is then used in conjunction with a substrate to be coated to form the ultra-thin layer. In many aspects of the invention, the coating composition is placed in contact with a surface of an article to be coated and then the composition and target surface of the article is irradiated to activate the photo-reactive groups of the photo-polymer to form the coated layer.

The coating methods described herein can be performed a number of ways, but generally, the formation of the ultra-thin layer includes an "in-solution" step wherein the coating composition contacts the substrate and then treated with irradiation to form the coating. For example, a coating solution is placed in contact with the surface of a substrate and then the substrate is irradiated before any significant portion of the composition is lost through evaporation of the liquid component of the composition.

The surface of the substrate can optionally be pre-treated prior to being placed in contact with the coating composition. In many cases the pre-treatment can facilitate the step wherein the coating composition is placed in contact with the surface. For example, all or a portion of the hydrophobic surface can be pre-wetted with a water miscible solvent such as an alcohol. Pre-wetting can be performed for any period of time, but generally, a short period of pre-wetting (seconds) is sufficient. For example, with a filter, pre-wetting can be performed by drawing the pre-wetting fluid through the filter under vacuum.

In the least, the coating composition includes the hydrophilic photo-polymer in a suitable liquid; other components can be optionally added. A coating composition can be prepared by dissolving a photo-polymer in a coating liquid, wherein the photo-polymer is present at a concentration sufficient by itself or in conjunction with other coating materials, to form the ultra-thin coated layer on the surface of the substrate. For example, in many embodiments the photo-polymer can be dissolved at a concentration in the range of about 0.01 to about 50 mg/mL. One photo-polymer, more than one photo-polymer, or a combination of one or more photo-polymers with one or more non-photo polymers can be combined to provide a coating composition with a polymer concentration in this range. More specific exemplary ranges are from about 0.1 mg/mL to about 10 mg/mL, and from about 0.5 mg/mL to about 5.0 mg/mL. For example, and as demonstrated herein, compositions including photo-poly(acrylamide), or photo-poly(acrylamide) and a non-photo polymer, were prepared at a concentration of 1 mg/mL and used to form an ultra-thin polymeric coating.

Suitable liquids for the coating composition can be aqueous liquids, non-aqueous liquids, or mixtures thereof. The term "aqueous" indicates that the main component of the liquid is water. However, an aqueous liquid could have significant concentrations of other dissolved liquids, for example, water soluble liquids such as alcohols, acetone, dilute acids, etc. Specific examples include, diethylene glycol, methanol, ethanol, n-propanol, isopropanol (IPA), n-butanol, n-hexanol, 2-pyrrolidone, polyethylene glycol, propylene glycol, 1,4-butanediol, glycerol, triethanolamine, propionic acid, and acetic acid. An aqueous solution can also be basic or acidic, and can include any sort of suitable salt. In some cases, one or more salts can be included in the coating composition to promote the association of the photo-polymer with the hydrophobic surface.

The ultra-thin coating can be formed in many different ways. In some cases it may be desired to form an ultra-thin coated layer over the entire surface of the substrate. This can be performed by obtaining a liquid coating composition, immersing the substrate in the coating composition, and then irradiating the substrate over its entire surface to form an ultra-thin coated layer. Either or both the position of the substrate or the position of the light source can be adjusted to provide activating irradiation over the surface of the device, if necessary.

Another way of performing the coating process is to apply the coating composition to a portion of the surface of the substrate. For example, a drop of coating composition can be applied to a portion of the device to be coated, and then the device is irradiated, forming a coating only on the portion of the device that is in contact with the coating composition. For example, in the case that one surface of an electrode is to be coated, the coating composition can be applied to that surface and then the surface irradiated to form the ultra-thin coated layer. Surface tensions of the coating composition may allow the drop of coating composition to cover the entire surface of one side of the electrode.

In some cases, a temporary barrier may be created on the substrate surface to contain the coating composition and define the area that the ultra-thin coating is to be formed on. This can be useful for creating ultra-thin coatings on surfaces wherein a pattern, or more than one pattern, of coated polymer is desired.

In other cases, if the ultra-thin coating is to be formed on a portion of a substrate, light irradiation can be directed to that portion of the substrate to activate the photoreactive groups thereby promoting formation of the coating.

The step of activating the photo-groups to promote the formation of the ultra-thin coating is typically performed by using a source of irradiation (light source) sufficient to activate the photoreactive groups of the photopolymer. For example, the photoreactive groups can have activation wavelengths in the UV and visible portions of the spectrum, such as in the range of 100-700 nm, or 300-600 nm, or 200-400 nm, or 300-340 nm. Light sources typically used to activate photopolymers provide a source of UV irradiation, such as short wavelength UV. Preferred photoreactive groups are activated by UV radiation in the range of 330 nm to 340 nm. Light sources that provide output radiation sufficient to activate the photoreactive groups and promote formation of the coating can be used. Suitable light sources can incorporate, for example, metal halide bulbs, or other suitable bulbs that provide an activating source of irradiation. One suitable light source is a Dymax BlueWave™ Spot Cure System, which is commercially available from Dymax Corp. (Torrington, Conn.).

Generally, the ultra-thin coating is formed by "in-solution" irradiation of the substrate. In this method light travels through the solution to the surface of the device wherein the light activates the photoreactive groups of the photopolymers that are proximal to the surface of the device, promoting bond formation and formation of the ultra-thin coated layer. While any amount of coating solution can be covering a surface of the substrate intended to be coated, in order to most efficiently promote formation of the ultra-thin layer, one can minimize the distance that light needs to travel through the solution by controlling the amount of coating solution covering the surface of the substrate. For example, a standard amount of solution covering the surface of the device could be in the range of 1 mm to 10 mm in depth.

The amount of energy that is applied to the surface can vary depending on a number of factors, including the type and amount of photo-polymer used, the substrate material, and the type and amount of coating composition. In some aspects an amount of energy in the range of about 5 mJ/cm$^2$ to about 5000 mJ/cm$^2$ as measured at 335 nm, is applied to the surface; a more preferable range is from about 50 mJ/cm$^2$ to about 500 mJ/cm$^2$. Other ranges can be used in conjunction with the step of forming the coating.

After the substrate has been irradiated to form the ultra thin layer, the remaining coating composition can be removed, or the coating composition can be washed off using a wash solution.

In another aspect of the invention, a water-soluble crosslinking agent having pendent photoreactive groups can be used in methods for forming the ultra-thin coated layer. The crosslinking agent can be added to improve properties of the coating, such as durability. In forming the ultra-thin coating, the crosslinking agent can provide additional bonding between the hydrophilic polymers of the ultra-thin coated layer, thereby improving its durability.

In some aspects, the coating can be formed by including a water-soluble crosslinking agent having pendent photoreactive groups in the coating composition along with the hydrophilic polymer having pendent photoreactive groups. Alternatively, the water-soluble crosslinking agent can be used independently of the hydrophilic polymer to form the ultra-thin coated layer.

In some aspects, a coating composition is prepared that includes a hydrophilic polymer having pendent photoreactive groups and a water soluble crosslinking agent.

A substrate is then contacted with the coating composition having at least these two components, for example, by immersing the substrate in the coating composition. The composition and substrate can then be irradiated to form the ultra-thin coated layer.

Alternatively, the crosslinking agent can be placed in contact with the substrate after the substrate has been in contact with the hydrophilic photo-polymer. For example, the ultra-thin coating can be prepared by first contacting a substrate with a first coating composition that includes a hydrophilic polymer having pendent photoreactive groups; the coating composition is then treated to activate the photoreactive groups of the hydrophilic photo-polymer. Full or partial activation of the photoreactive groups can be performed. Optionally, one or more washing steps can be performed before the second coating composition is contacted to the substrate. After the step of irradiation, the first coating composition can be removed and a second coating composition that includes the crosslinking agent can be placed in contact with the substrate. Irradiation of the second coating composition and the substrate can then be performed.

Alternatively, after the first coating composition is irradiated, the crosslinking agent can be added to the first coating composition, and then a second irradiation step can be performed. In this aspect, the ultra-thin coated layer is formed after the first irradiation step, and the addition and subsequent irradiation of the crosslinking agent further crosslinks the ultra-thin coated layer. In some aspects, this method may save time and reagents, as various steps, washings, and/or compositions can be optionally eliminated.

Exemplary water-soluble cross-linking agents having photoreactive groups include ionic crosslinkers. Any suitable ionic photoactivatable cross-linking agent can be used. In some embodiments, the ionic photoactivatable cross-linking agent is a compound of formula I:

$$X_1-Y-X_2$$

where Y is a radical containing at least one acidic group, basic group, or a salt of an acidic group or basic group. $X_1$ and $X_2$ are each independently a radical containing a latent photoreactive group.

The photoreactive groups can be the same as those described for use with the hydrophilic polymer. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable cross-linking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate.

For example, compounds of formula I can have a Y radical that contains an ammonium group; $X_1$ and $X_2$ can contain photoreactive groups that include aryl ketones. Such photoactivatable cross-linking agents include ethylenebis(4-benzoylbenzyldimethylammonium) salt; hexamethylenebis(4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

After the ultra-thin coated layer has been formed on the surface of the device, it includes hydrophilic polymer having pendent photo-"reacted" groups, meaning that photoreactive groups had undergone activation and reaction with a target moiety, for example another hydrophilic polymer and/or the substrate surface, to form a covalent bond to immobilize the polymer.

The invention will be further described with reference to the following non-limiting Examples.

EXAMPLES

Preparation of Photopolymers

Photo-polyacrylamide (photo-PA) was prepared by copolymerizing a methacrylamide having a photoreactive group with acrylamide. The photoreactive monomer, N-[3-(4-Benzoylbenzamido)propyl]methacrylamide, was prepared according to the process described in U.S. Pat. No. 5,858,653 (see Example 3).

Photo-poly(vinylpyrrolidone) (photo-PVP) was made by the copolymerization of 1-vinyl-2-pyrrolidone (Aldrich) and N-(3-aminopropyl)methacrylamide (APMA), followed by photoderivatization of the polymer using 4-benzoylbenzoyl chloride, as described in Example 22 of U.S. Pat. No. 6,077,698, under Schotten-Baumann conditions (a two phase aqueous/organic reaction system). APMA was prepared as described in Example 2 of U.S. Pat. No. 5,858,653.

Example 1

A thin photo-polymer coating was formed on a hydrophobic substrate having small pores. Specifically, expanded PTFE (ePTFE) membranes were coated with photo-polyacrylamide to provide a very thin hydrophilic coating over the membrane material. An expanded PTFE membrane having a 0.2 micron (average) pore size and 47 mm diameter (Donaldson, Inc., Minneapolis, Minn.) was wetted with 2 mL isopropanol two times for a few seconds at room temperature. Excess isopropanol was removed with an aspirator vacuum after each wetting. Photo-PA (30-50 kDa MW) (SurModics, Inc., Eden Prairie, Minn.) was prepared at a concentration of 1 mg/mL in water, and 2 mL of the photo-PA solution were pulled quickly (2 sec) through the ePTFE membrane under vacuum. The vacuum process was repeated an additional three times, but with 4 mL of photo-PA solution at each time. The ePTFE membrane was then immersed in 4 mL of the photo-PA solution leaving approximately 1 mm of solution covering the membrane and illuminated for 60 seconds using an ultraviolet Dymax™ Cure System (light system commercially available from Dymax; Torrington, Conn.) at a distance of 20 cm. This distance and time provided the membrane with approximately 100 mJ/cm$^2$ in the wavelength range 330-340 nm. During illumination, the membrane was kept wet and not allowed to dry. After illumination, the membrane was removed from the photo-PA solution, washed with water by vacuum, and dried at 55° C. for 15 minutes. The coated membrane demonstrated complete rewetting when immersed in water (as compared to the un-coated membranes), indicating the presence of a photo-PA coating on the membrane.

The photo-PA-coated ePTFE membrane was imaged using scanning electron micrography (SEM) and compared to an ePTFE membrane having polymer coating. The membranes were imaged at 10 k X at using an accelerating voltage of 0.85 kV. The SEM micrographs show that the membrane size of the photo-PA coated ePTFE membrane and the uncoated membrane are substantially the same.

Example 2

The photo-PA-coated ePTFE membrane as prepared in Example 1 was tested to determine its affect on the flow of water (flux).

Flux was measured using an aspirator vacuum at a pressure of 100 mm. Hg (0.13 ATM). 10 mL of water was placed on the coated membrane and the vacuum was applied to draw the water through the coated membrane. 10 mL of water was completely pulled through the membrane in 17 seconds. Following this, an additional 100 mL of water was pulled through the membrane under vacuum, and then the membrane was allowed to dry. After drying, an additional 10 mL of water was pulled through the filter under the same vacuum. This time, the 10 mL of water was completely pulled through the membrane in 10 seconds. Water could not be drawn through an uncoated membrane using the pressure as indicated above.

Example 3

Wetting and coating of the ePTFE membrane was performed as described in Example 1 except that the coating composition was a mixture of photo-polyacrylamide at a concentration of 0.95 mg/mL and polyvinylpyrrolidone (Kollidon™ 30, BASF; PVP) at a concentration of 0.05 mg/mL in water. After illumination, the membrane was removed from the photo-PA/PVP solution, washed with water by vacuum, and dried at 120° C. for 15 minutes. The photo-PA/PVP-coated membranes were completely wettable after drying at 120° C.

The photo-PA/PVP-coated ePTFE membrane was imaged using scanning electron micrography (SEM) as described in Example 1. The SEM micrographs show that the membrane size of the photo-PA/PVP-coated ePTFE membrane and the uncoated membrane are substantially the same, further indicating that the coating on the membrane held up well to higher temperatures. Use of a higher temperature also indicates that the coated membrane can be heat sterilized without loss of the hydrophilic properties of the coating.

Example 4

The photo-PA/PVP-coated ePTFE membrane as prepared in Example 3 was tested to determine its affect on the flow of water (flux).

Flux was measured according the process carried out in Example 2. 10 mL of water was completely pulled through the membrane in 20 seconds.

Example 5

Wetting and coating of the ePTFE membrane was performed as described in Example 1 except that the coating composition was a mixture of photo-polyacrylamide at a concentration of 0.95 mg/mL and photo-PVP at a concentration of 0.05 mg/mL in water. The membranes were also washed and dried as detailed in Example 3. The photo-PA/photo-PVP-coated membranes were completely wettable after drying at 120° C. This membrane was also tested to determine its affect on the flow of water.

Example 6

A polypropylene substrate provided with an ultra thin coating of photo-PVP and then tested for the ability of the coating to wick water. A 50 mm thick melt blown polypropylene (Daramic Corp., Owensboro, Ky.) was saturated with a solution of photo-PVP at 1 mg/mL in a 99.4% water/0.6% hexanol V/V mixture. The saturated material was illuminated for 1 minute under a Dymax™ light, removed from the coating solution, and then allowed to dry. The resulting material was permanently wettable with water as demonstrated by its ability to wick water repeatedly. This material wicks water to the height of 1 inch in 10 seconds.

Wicking was compared to polypropylene substrates that were irradiated after (post-solution irradiation) the polypropylene was dipcoated in the photo-deviratized polyvinylpyrrolidone solution. In this case, the coating solution that was dip-coated on to the polypropylene was allowed to dry before illumination. For these post-solution irradiated samples, the coated substrates did not wick water.

Example 7

The hydrophilic photo-polymer coatings were examined by atomic force microscopy to determine their thickness.

Soda lime glass microscope slides (Erie Scientific, Portsmouth, N.H.) were silane treated by dipping in a mixture of p-tolyldimethylchlorosilane (1% w/v) and n-decyldimethylchlorosilane (1% w/v; United Chemical Technologies, Bristol, Pa.) in acetone. After air drying, the slides were cured at 120° C. for 1 hour. Slides were then washed with acetone followed by dipping in DI water and drying. The slides were submerged to a depth of approximately 1 mm in a solution of either photo-PA or photo-PVP at 1 mg/mL in water and illuminated for 1 minute under a Dymax lamp to deliver approximately 100 mJ/cm$^2$.

Slides were washed with water and spun dry in a centrifuge. Presence of the coating was ascertained by water contact angle using a Kruss DSA 10 goniometer (Hamburg, Germany). The base silane had a contact angle of 72.8±0.4°. The photo-PA coating was 17.5±2.4° and the photo-PVP was 25.1±3.7°. The thickness of these coatings was measured by atomic force microscopy (AFM). The coating was cut using a brass blade and the resulting step height measured using contact mode AFM. The photo-poly(acrylamide) was measured at 2.4±0.5 nm and the photo-PVP at 1.5±0.3 nm. Errors are standard deviation.

What is claimed is:

1. A device having a hydrophilic polymeric coating having a thickness of 20 nm or less, the coating comprising a plurality of hydrophilic polymers covalently bonded via pendent photo-reactive groups; wherein the pendent photo-reactive groups have been reacted to form the hydrophilic polymeric coating; and wherein the coating is formed by a process comprising contacting a substrate with a coating composition comprising a hydrophilic polymer comprising at least one pendent latent photoreactive group, wherein the photoreactive group comprises an aryl ketone selected from the group consisting of acetophenone, benzophenone, anthraquinone, anthrone, and substituted derivatives thereof, and while the coating composition is in contact with the substrate, irradiating the composition to activate the pendent latent photoreactive groups to form the hydrophilic polymeric coating.

2. The device of claim 1, wherein the device is a filter having an average pore size of 5 μm or less.

3. The device of claim 1, wherein the device is a biosensor.

4. The device of claim 1 wherein the hydrophilic polymeric coating has a thickness of 5 nm or less.

5. The device of claim 1 wherein the photoreactive groups are activated by radiation having a wavelength in the range of 200 nm to 400 nm.

6. The device of claim 1 wherein the photoreactive groups are activated by UV radiation in an amount in the range of 5 mJ/cm2 to 5000 mJ/cm2.

7. The device of claim 6 wherein the photoreactive groups are activated by UV radiation in an amount in the range of 50 mJ/cm2 to 500 mJ/cm2.

8. The device of claim 1 wherein the photoreactive group comprises an aryl ketone.

9. The device of claim 1 wherein the substrate comprises micro-structured or nano-structured features.

10. The device of claim 1 wherein the substrate is selected from the group of articles having fibers, pores, filaments, threads, processes, or apertures, or combinations thereof.

11. The device of claim 10 wherein the substrate comprises pores.

12. The device of claim 11 wherein the substrate comprises pores having an average size of 5 μm or less.

13. The device of claim 12 wherein the substrate comprises pores having an average size in the range of 0.05 μm to 5 μm.

14. The device of claim 1 wherein the substrate is selected from the group consisting of silicon materials, silver surfaces having organic molecules, chemically stable semiconductor layers, cluster/molecule/semiconductor assemblies, cluster networks, micro-electro-mechanical-systems (MEMS), actuators, micro-and nano-scale integrated systems, microfluidic bio-chips, micro-flow systems, and nano-electronic devices for DNA characterization.

15. The device of claim 1 wherein the substrate comprises an implantable medical device.

16. The device of claim 1 wherein the substrate comprises a filter.

17. The device of claim 1 wherein the coating is placed in contact with a substrate having a hydrophobic surface and that is a poor source of, or provides no abstractable hydrogens.

18. . The device of claim 17 wherein the hydrophobic surface comprises a halogen-containing polymeric material.

19. The device of claim 18 wherein the hydrophobic surface comprises a chloro-or floro-saturated polymer.

20. The device of claim 19 wherein the hydrophobic surface comprises PTFE.

21. The device of claim 1 wherein the coating composition comprises a water soluble crosslinking agent having pendent photoreactive groups.

22. The device of claim 1 wherein the hydrophilic polymer has a molecular weight of 500 kDa or less.

23. The device of claim 1 wherein the hydrophilic polymer has a molecular weight in the range of 10 kDa to 500 kDa.

24. The device of claim 1 wherein the hydrophilic polymer is present in the coating composition at a concentration in the range of 0.01 mg/mL to 50 mg/mL.

25. The device of claim 24 wherein the hydrophilic polymer is present at a concentration in the range of 0.1 mg/mL to about 10 mg/mL in the coating composition.

26. The device of claim 1 wherein the coating composition is an aqueous composition.

27. The device of claim 1, wherein the substrate is a plastic article.

28. The device of claim 1, wherein the device is a microfluidic channel device.

29. The device of claim 1, wherein the device is a medical article.

30. A device comprising
   (i) a substrate that is a poor source of, or provides no abstractable hydrogens; and
   (ii) a hydrophilic polymeric coating applied to a surface of the substrate, the coating having a thickness of 20 nm or less comprising a plurality of hydrophilic polymers covalently bonded via pendent photo-reactive groups; wherein the pendent photo-reactive groups have been reacted to form the hydrophilic polymeric coating; wherein the coating is formed by a process comprising contacting the substrate with a coating composition comprising a hydrophilic polymer comprising at least one pendent latent photoreactive group, wherein the photoreactive group comprises an aryl ketone selected from the group consisting of acetophenone, benzophenone, anthraquinone, anthrone, and substituted derivatives thereof, and irradiating the composition to activate the pendent latent photoreactive groups to form the hydrophilic polymeric coating.

31. The device of claim 1 wherein the photoreactive group is attached to the hydrophilic polymer via an amide bond.

32. The device of claim 31 wherein the amide bond is formed from an N-(3-aminopropyl) moiety of a hydrophilic polymer.

33. The device of claim 1 wherein the hydrophilic polymer comprises aminoalkyl(meth)acrylamide and the photoreactive group is attached to the polymer via the aminoalkyl (meth)acrylamide.

34. The device of claim 1 wherein the hydrophilic polymer comprises from a photoreactive group-monomer in an amount in a range from 0.1% to about 10%, and a hydrophilic monomer, or combination of hydrophilic monomers, in an amount in a range from 90% to about 99.9%, as based on a molar percentage.

35. The device of claim 1 wherein the hydrophilic polymer comprises a monomer selected from the group consisting of methacrylate, methyl methacrylate, hydroxyethyl methacrylate, hydroxyethyl acrylate, methacrylic acid, acrylic acid, glycerol acrylate, glycerol methacrylate, acrylamide, methacrylamide, vinyl acetate, vinylpyrrolidone, vinyl alcohol, ethylene oxide, propylene oxide, and butylene oxide.

36. The device of claim 35 wherein the hydrophilic polymer comprises poly(vinyl pyrrolidone) or a copolymer of vinyl pyrrolidone and a monomer selected from the group consisting of hydrophilic monomers.

37. The device of claim 36 comprising a copolymer of vinyl pyrrolidone and a monomer selected from (meth)acrylamide, alkyl(meth)acrylamide, and aminoalkyl(meth)acrylamide.

38. An implantable medical device having a hydrophilic polymeric coating having a thickness of 20 nm or less, the coating comprising a plurality of hydrophilic polymers covalently bonded via pendent photo-reactive groups; wherein the pendent photo-reactive groups have been reacted to form the hydrophilic polymeric coating; and wherein the coating is formed by a process comprising contacting an implantable medical device with a coating composition comprising a hydrophilic polymer comprising at least one pendent latent photoreactive group, wherein the photoreactive group comprises an aryl ketone selected from the group consisting of acetophenone, benzophenone, anthraquinone, anthrone, and substituted derivatives thereof, and while the coating composition is in contact with the device, irradiating the composition to activate the pendent latent photoreactive groups to form the hydrophilic polymeric coating.

39. An implantable medical device having a hydrophilic polymeric coating having a thickness of 20 nm or less, the coating comprising a plurality of hydrophilic polymers covalently bonded via pendent photo-reactive groups; wherein the pendent photo-reactive groups have been reacted to form the hydrophilic polymeric coating; and wherein the coating is formed by a process comprising contacting an implantable medical device with a coating composition comprising a hydrophilic polymer comprising at least one pendent latent photoreactive group, wherein the hydrophilic polymer comprises aminoalkyl(meth)acrylamide and the photoreactive group is attached to the polymer via the aminoalkyl(meth)acrylamide, and while the coating composition is in contact with the device, irradiating the composition to activate the pendent latent photoreactive groups to form the hydrophilic polymeric coating.

40. The implantable medical device of claim 39 wherein the photoreactive group comprises an aryl ketone selected from the group consisting of acetophenone, benzophenone, anthraquinone, anthrone, and substituted derivatives thereof.

* * * * *